(12) United States Patent
Rodstrom et al.

(10) Patent No.: US 8,753,666 B2
(45) Date of Patent: Jun. 17, 2014

(54) PUNCTAL PLUGS AND METHODS OF DELIVERING THERAPEUTIC AGENTS

(75) Inventors: Theron R. Rodstrom, Cranfills Gap, TX (US); Larry Smith, II, Glen Rose, TX (US); Youqin Tian, Colleyville, TX (US); David Allen Marsh, Fort Worth, TX (US); Alan L. Weiner, Arlington, TX (US); Shivalik Bakshi, Boston, MA (US)

(73) Assignee: Alcon Research, Ltd., Fort Worth, TX (US)

( * ) Notice: Subject to any disclaimer, the term of this patent is extended or adjusted under 35 U.S.C. 154(b) by 1169 days.

(21) Appl. No.: 12/022,520

(22) Filed: Jan. 30, 2008

(65) Prior Publication Data

US 2008/0181930 A1 Jul. 31, 2008

Related U.S. Application Data

(60) Provisional application No. 60/898,599, filed on Jan. 31, 2007.

(51) Int. Cl.
*A61F 2/00* (2006.01)
*A61K 9/14* (2006.01)
*A61K 51/00* (2006.01)
*A61M 36/14* (2006.01)

(52) U.S. Cl.
USPC ........... 424/427; 424/423; 424/484; 424/1.25

(58) Field of Classification Search
None
See application file for complete search history.

(56) References Cited

U.S. PATENT DOCUMENTS

| | | | |
|---|---|---|---|
| 3,949,750 A | 4/1976 | Freeman | 128/260 |
| 3,992,518 A | 11/1976 | Chien et al. | 424/22 |
| 4,053,580 A | 10/1977 | Chien et al. | 424/15 |
| 4,660,546 A | 4/1987 | Herrick et al. | 128/1 R |
| 4,690,931 A | 9/1987 | Wick et al. | 514/317 |
| 4,915,684 A | 4/1990 | MacKeen et al. | 604/8 |
| 4,923,699 A | 5/1990 | Kaufman | 424/427 |
| 4,959,048 A | 9/1990 | Seder et al. | 604/9 |
| 5,049,142 A | 9/1991 | Herrick et al. | 604/294 |
| 5,053,030 A | 10/1991 | Herrick et al. | 604/890.1 |
| 5,067,491 A * | 11/1991 | Taylor et al. | 600/561 |
| 5,151,444 A | 9/1992 | Ueno et al. | 514/530 |
| 5,163,959 A | 11/1992 | Herrick | 623/11 |
| 5,171,270 A | 12/1992 | Herrick | 623/11 |
| 5,283,063 A | 2/1994 | Freeman | 424/427 |
| 5,296,504 A | 3/1994 | Stjernschantz et al. | 514/530 |
| 5,352,708 A | 10/1994 | Woodward et al. | 514/729 |
| 5,378,475 A | 1/1995 | Smith et al. | 424/473 |
| 5,417,651 A | 5/1995 | Guena et al. | 604/8 |
| 5,422,368 A | 6/1995 | Stjernschantz et al. | 514/530 |
| 5,423,777 A | 6/1995 | Tajiri et al. | 604/294 |
| 5,469,867 A | 11/1995 | Schmitt | 128/898 |
| 5,723,005 A | 3/1998 | Herrick | 623/4 |
| 5,731,005 A | 3/1998 | Ottoboni et al. | 424/499 |
| 5,741,292 A | 4/1998 | Mendius | 606/191 |
| 5,773,019 A | 6/1998 | Ashton et al. | 424/423 |
| 5,826,584 A | 10/1998 | Schmitt | 128/898 |
| 5,830,171 A | 11/1998 | Wallace | 604/8 |
| 5,840,054 A | 11/1998 | Hamano et al. | 604/8 |
| 5,889,052 A | 3/1999 | Klimko et al. | 514/530 |
| 6,001,386 A | 12/1999 | Ashton et al. | 424/423 |
| 6,016,806 A | 1/2000 | Webb | 128/846 |
| 6,027,470 A | 2/2000 | Mendius | 604/8 |
| 6,041,785 A | 3/2000 | Webb | 128/887 |
| 6,149,684 A | 11/2000 | Herrick | 623/4.1 |
| 6,196,993 B1 * | 3/2001 | Cohan et al. | 604/891.1 |
| 6,234,175 B1 | 5/2001 | Zhou et al. | 128/887 |
| 6,290,684 B1 | 9/2001 | Herrick | 604/294 |
| 6,306,114 B1 | 10/2001 | Freeman et al. | 604/9 |
| 6,344,047 B1 | 2/2002 | Price et al. | 606/191 |
| 6,383,192 B1 | 5/2002 | Kurihashi | 606/108 |
| 6,605,108 B2 * | 8/2003 | Mendius et al. | 623/1.11 |
| 7,117,870 B2 | 10/2006 | Prescott | 128/898 |
| 7,204,995 B2 | 4/2007 | El-Sherif et al. | 424/427 |
| 7,510,541 B2 * | 3/2009 | Hanna | 604/9 |
| 2002/0022055 A1 | 2/2002 | Signore | 424/486 |
| 2002/0106411 A1 | 8/2002 | Wironen et al. | 424/489 |
| 2002/0128613 A1 | 9/2002 | Nakayama | 604/294 |
| 2002/0151960 A1 | 10/2002 | Mendius et al. | |
| 2002/0198453 A1 | 12/2002 | Herrick, II | 600/431 |
| 2004/0013704 A1 | 1/2004 | Kabra et al. | 424/427 |

(Continued)

FOREIGN PATENT DOCUMENTS

EP 0 561 073 10/2001
JP 9276318 10/1997

(Continued)

OTHER PUBLICATIONS

SCS Coatings (SCS Coatings website, SCS Parylene Properties and Parylene History, 2014).*
PCT International Search Report for corresponding PCT/US2008/052439 with mailing date Mar. 3, 2009.
PCT Written Opinion of the International Searching Authority for corresponding PCT/US2008/052439 with mailing date Mar. 3, 2009.
Meng and Tai, "Parylene Etching Techniques for Microfluidics and BioMEMS," *Micro Electro Mechanical Systems*, 30:568-571, 2005.
FCI Ophthlamics Product Catalog, 2007.

*Primary Examiner* — Brian-Yong Kwon
*Assistant Examiner* — Mark V Stevens
(74) *Attorney, Agent, or Firm* — Scott A. Chapple

(57) ABSTRACT

The present invention concerns implantable ocular devices for the sustained release of medication to the eye, and methods for manufacturing and using such devices. In one embodiment, the present invention provides a device comprising: (a) a body comprising a matrix of a prostaglandin and a silicone; (b) a parylene coating on the outer surface of the body; and (c) one or more pores extending from the outer surface of the parylene coating to the outer surface of the body.

23 Claims, 4 Drawing Sheets

(56) References Cited

U.S. PATENT DOCUMENTS

| | | | |
|---|---|---|---|
| 2004/0022853 A1 | 2/2004 | Ashton et al. | 424/468 |
| 2004/0043067 A1* | 3/2004 | Salamone et al. | 424/468 |
| 2004/0146546 A1 | 7/2004 | Gravett et al. | 424/445 |
| 2004/0175426 A1 | 9/2004 | Ashton | 424/471 |
| 2004/0176749 A1 | 9/2004 | Lohmann et al. | 604/891.1 |
| 2005/0015143 A1* | 1/2005 | Willis et al. | 623/6.36 |
| 2005/0232972 A1 | 10/2005 | Odrich | 424/427 |
| 2005/0244464 A1* | 11/2005 | Hughes | 424/427 |
| 2006/0020248 A1 | 1/2006 | Prescott | 604/294 |
| 2006/0029721 A1* | 2/2006 | Chappa | 427/2.1 |
| 2006/0122553 A1 | 6/2006 | Hanna | |
| 2006/0147492 A1* | 7/2006 | Hunter et al. | 424/426 |
| 2006/0246145 A1 | 11/2006 | Chang et al. | 424/490 |
| 2007/0269487 A1* | 11/2007 | de Juan et al. | 424/427 |
| 2007/0298075 A1 | 12/2007 | Borgia et al. | 424/428 |
| 2007/0299516 A1 | 12/2007 | Cui et al. | 623/4.1 |
| 2008/0045911 A1 | 2/2008 | Borgia et al. | 604/294 |
| 2008/0086101 A1 | 4/2008 | Freilich | 604/294 |

FOREIGN PATENT DOCUMENTS

| | | |
|---|---|---|
| JP | 10033584 | 2/1998 |
| WO | 94/13275 | 6/1994 |
| WO | 99/37260 | 7/1999 |
| WO | 00/50016 | 8/2000 |
| WO | 00/62760 | 10/2000 |
| WO | 02/11783 | 2/2002 |
| WO | 02055058 A2 | 7/2002 |
| WO | 02/083198 | 10/2002 |
| WO | 2004/066980 | 8/2004 |
| WO | 2004098565 A2 | 11/2004 |
| WO | 2006/014434 | 2/2006 |
| WO | 2006/031658 | 3/2006 |
| WO | 2007/115259 | 10/2007 |
| WO | 2007/115261 | 10/2007 |

\* cited by examiner

Fig. 4
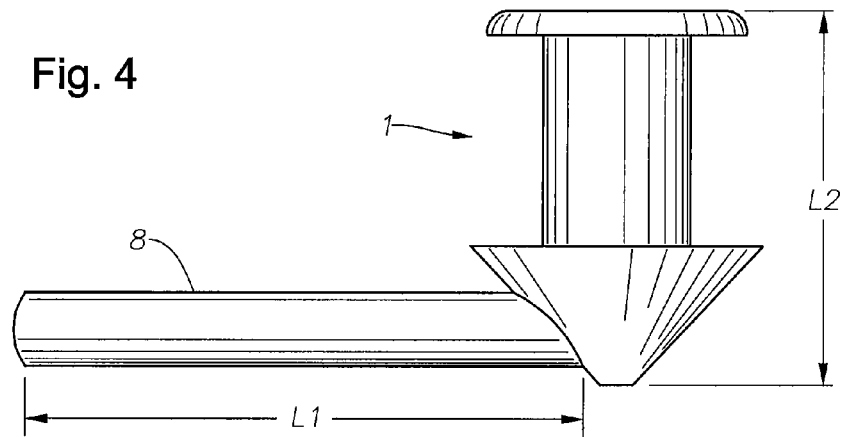
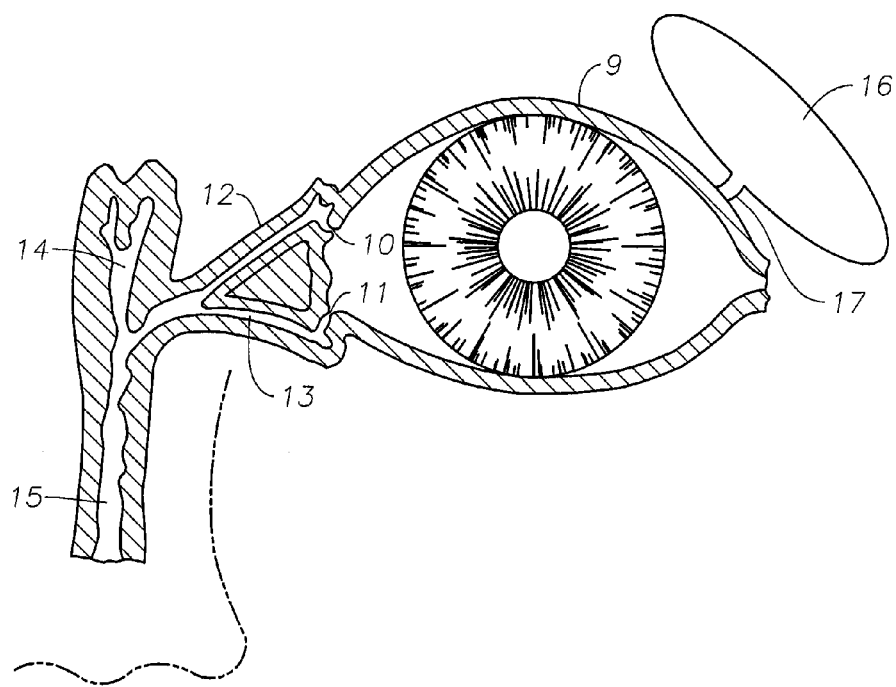
Fig. 5

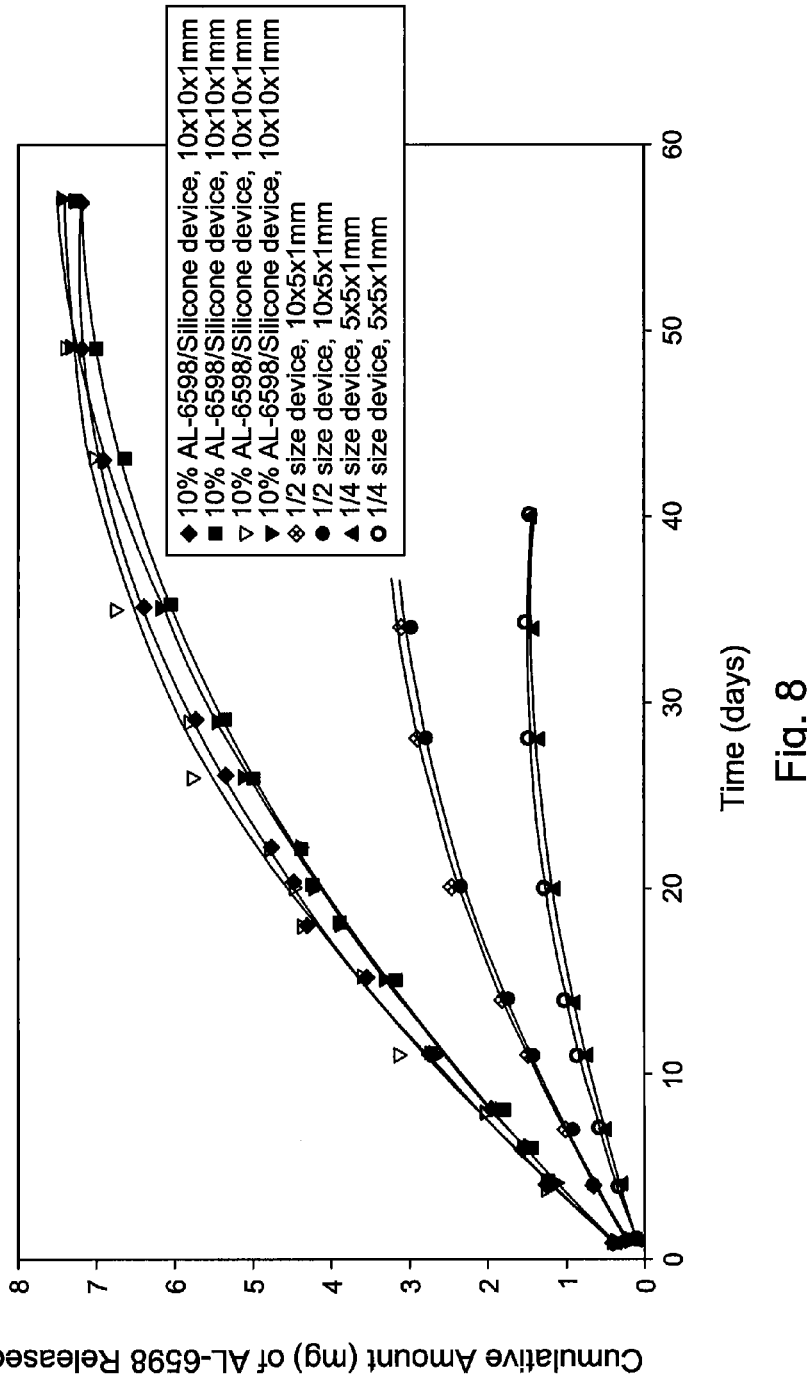

PUNCTAL PLUGS AND METHODS OF DELIVERING THERAPEUTIC AGENTS

This application claims priority to U.S. Provisional Application, U.S. Ser. No. 60/898,599 filed Jan. 31, 2007.

BACKGROUND OF THE INVENTION

1. Field of the Invention

The present invention relates generally to the fields of implantable ocular devices, pharmaceutics, and methods of drug delivery to the eye. More particularly, it concerns implantable ocular devices for the sustained delivery of a therapeutic compound to the eye.

2. Description of Related Art

Glaucoma is the leading cause of blindness worldwide. It is the most common cause of optic neuropathy.

One major risk factor for developing glaucoma is family history. Several different inherited forms of glaucoma have been described. Primary congenital or infantile glaucoma is an inherited disorder that is characterized by an improper development of the aqueous outflow system of the eye, which leads to elevated intraocular pressure and damage to the optic nerve.

Open angle glaucoma is a common disorder characterized by atrophy of the optic nerve resulting in visual field loss and eventual blindness. Open angle glaucoma has been divided into two major groups, based on age of onset and differences in clinical presentation. Juvenile-onset open angle glaucoma (JOAG) usually manifests itself in late childhood or early adulthood. Adult- or late-onset primary open angle glaucoma (POAG) is the most common type of glaucoma. It is milder and develops more gradually than JOAG, with variable onset usually after the age of 40. POAG is associated with slight to moderate elevation of intraocular pressure, and often responds satisfactorily to regularly monitored medical treatment. Unfortunately, this disease may not be detected until after irreversible damage to the optic nerve has already occurred because it progresses gradually and painlessly.

Ocular hypertension is a condition wherein intraocular pressure is elevated but no apparent loss of visual function has occurred; such patients are considered to be at high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven useful for the reduction of intraocular pressure include both agents that decrease aqueous humor production and agents that increase the outflow facility. Such therapies are in general administered by one of two possible routes, topically (direct application to the eye) or orally.

Examples of agents used for treating glaucoma include β-blockers (e.g., timolol, betaxolol, levobetaxolol, carteolol, levobunolol, propranolol), carbonic anhydrase inhibitors (e.g., brinzolamide and dorzolamide), α1 antagonists (e.g., nipradolol), α2 agonists (e.g. iopidine and brimonidine), miotics (e.g., pilocarpine and epinephrine), prostaglandin analogs (e.g., latanoprost, travoprost, unoprostone, and compounds set forth in U.S. Pat. Nos. 5,889,052; 5,296,504; 5,422,368; and 5,151,444), "hypotensive lipids" (e.g., bimatoprost and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 60/203,350, and appropriate compounds from WO 94/13275, including memantine.

One of the limitations of topical therapy is inadequate and irregular delivery of the therapeutic agent to the eye. For example, when an eye drop is applied to the eye, a substantial portion of the drop may be lost due to overflow of the lid margin onto the cheek.

Various ocular drug delivery implants have been described in an effort to improve and prolong drug delivery. For example, U.S. Pat. No. 3,949,750 discloses a punctal plug made of a tissue-tolerable, readily sterilizable material, such as Teflon, HEMA, hydrophilic polymer, methyl methacrylate, silicone, stainless steel or other inert metal material. It is stated that the punctal plug may be impregnated with ophthalmic medication or that the punctal plug may contain a reservoir of the ophthalmic drug.

U.S. Pat. No. 5,053,030 discloses an intracanalicular implant that can be used as a carrier or medium for distributing medications throughout the body. U.S. Pat. No. 5,469,867 discloses a method of blocking a channel, such as the lacrimal canaliculus by injecting a heated flowable polymer into the channel and allowing it to cool and solidify. The polymer may be combined with a biologically active substance that could leach out of the solid occluder once it has formed in the channel.

WO 99/37260 discloses a punctal plug made of a moisture absorbing material, which is not soluble in water, such as a modified HEMA. It is also disclosed that an inflammation inhibitor, such as heparin, may be added to the material from which the punctal plug is made.

U.S. Pat. No. 6,196,993 discloses a punctal plug containing glaucoma medication. The medication is contained in a reservoir within the plug. The reservoir is in fluid communication with a pore through which the medication is released onto the eye.

U.S. Pub. No. 2003/0143280 discloses the use of biodegradable polymer capsules fro treating ophthalmic disorder including dry eye and glaucoma. The capsules are made of any biodegradable, biocompatible polymer and may contain a treating agent.

U.S. Pub. No. 2004/0013704 discloses solid or semi-solid implant compositions lacking polymeric ingredients. These implant compositions are made of lipophilic compounds and may be implanted anywhere in the eye including the punctum or lacrimal canaliculous. It is stated that the implants may contain any ophthalmic drug, including anti-glaucoma drugs.

WO 2004/066980 discloses a device for delivering a carbonic anhydrase inhibitor (CAI) to the eye over an extended period of time. In one embodiment, the device has an inner CAI-containing core and an outer polymeric layer. The outer layer may be permeable, semi-permeable, or impermeable to the drug. Where the outer layer is impermeable to the drug, it may have one or more openings to permit diffusion of the CAI.

U.S. Pub. No. 2005/0232972 discloses ocular implants to which active agents have been applied to at least one surface. In one embodiment, the implant may contain a hollow core filled with medication. In another embodiment, the medication may be applied to one or more bands of polymer material. Alternatively, a porous or absorbent material can be used to make up the entire plug or implant which can be saturated with the active agent.

WO 2006/031658 discloses lacrimal canalicular inserts including a polymer component and a therapeutic component. The polymer component may include one or more non-biodegradable polymers, one or more biodegradable polymers, or combinations thereof. The insert may comprise a matrix of a polymer component and a therapeutic component. The inserts may be coated with a substantially impermeable coating.

U.S. Pub. No. 2006/0020248 discloses an ophthalmological device for lacrimal insertion that includes a reservoir for a medication, such as a glaucoma, antimicrobial, anti-inflammatory, or dry-eye syndrome medication.

A reservoir drug-delivery device is a device that contains a receptacle or chamber for storing the drug. There are drawbacks to reservoir drug delivery devices in that they are difficult to manufacture, difficult to achieve drug content uniformity (i.e., device to device reproducibility, particularly with small ocular devices), and they carry the risk of a "dose dump" if they are punctured. In matrix drug delivery devices the drug is dispersed throughout a polymeric matrix and is released as it dissolves or diffuses out of the matrix. Matrix devices have an advantage over reservoir devices in that they are not subject to a dose dump if punctured. A disadvantage of matrix devices is that it can be difficult to achieve zero-order drug release kinetics. Zero-order drug release or near zero-order drug release is desirable because the rate of drug release is independent of the initial concentration of the drug, thus the drug can be released at therapeutic levels over a sustained period of time. The manufacture of matrix devices can also present difficulties when the drug and the polymer are processed and extruded at elevated temperature and/or pressure as this may reduce the activity of the drug.

The devices of the present invention address these deficiencies in the art by providing matrix devices that achieve zero-order or near zero-order drug-release kinetics typically associated with reservoir devices, but without the risk of dose dumping and the manufacturing difficulties of reservoir devices.

SUMMARY OF THE INVENTION

In one embodiment, the present invention provides a drug-delivery device comprising: (a) a body comprising a matrix of a hydrophobic flexible polymer and a therapeutic compound; (b) a coating located on the outer surface of the first member, the coating comprising a second non-biodegradable polymer that is substantially impermeable to the therapeutic compound; and (c) at least one pore extending from the outer surface of the coating to the outer surface of the body. The devices of the present invention may be configured for implantation at any location within the body of a subject. In particular embodiments, the device is configured for implantation in the punctum, lacrimal canaliculus, sub-conjunctiva space, anterior sub-Tenon space, or any other location suitable for release of medication on to the eye of the subject. For example, for delivering a therapeutic compound to the eye, a device of the present invention may be configured as a punctal plug, lacrimal insert, or fornix device.

The hydrophobic flexible polymer may be, for example, a silicone, a polyacrylate, polyurethane, or a combination of two or more of these polymers. The silicone may be any unrestricted silicone suitable for injection, compression, or transfer molding. Non-limiting examples of commercially available, unrestricted silicones that may be used in making the devices of the present invention include MED-4870, MED-4830, MED-4840, MED-4850, MED-4860, or MED-4880 (NuSil Technology LLC). Non-limiting examples of Non-limiting examples of polyacrylates include polymers of 2-hydroxyethylmethacrylate (HEMA), methacrylic acid (MA), methyl methacrylate (MMA). The therapeutic compound may be any therapeutic compound, so long as the therapeutic compound is dispersible or miscible in the polymer matrix (e.g., a silicone matrix). The dispersion may be of solid particles or oil. In particular embodiments, the therapeutic compound is a compound that can be applied for the treatment of an ophthalmic disorder. For example, the therapeutic compound may be a glaucoma medication, an antimicrobial medication, an anti-inflammatory medication, or a dry-eye syndrome medication, or a therapeutic compound that can be applied in the treatment of diabetic retinopathy or age-related macular degeneration. Highly potent ophthalmic drugs, such as prostaglandins, triamcinolone, 15-HETE (Icomucret), and rimexolone, are well suited for delivery with the devices of the present invention. The prostaglandin may be a natural or a synthetic prostaglandin. Non-limiting examples of prostaglandins include cloprostenol, fluprostenol, latanoprost, travoprost, and unoprostone.

In certain aspects of the invention, the concentration of the prostaglandin in the matrix is between about 0.5% to about 15%, about 1% to about 10%, about 1% to about 9%, about 1% to about 8%, about 1% to about 7%, about 3% to about 7%, about 1% to about 6%, about 1% to about 5%, about 5% to about 10%, or about 2.5% to about 7.5% by weight.

The coating located on the outer surface of the body of the device comprises a second non-biodegradable polymer that is substantially impermeable to the therapeutic compound, or is at least less permeable to the therapeutic compound than the therapeutic compound is to the first non-biodegradable polymer. In one embodiment, the coating has a thickness of between about 0.5 nanometers (nm) to about 100 micrometers ($\mu$m), about 100 nm to about 50 $\mu$m, about 1 $\mu$m to about 20 $\mu$m, about 5 $\mu$m to about 15 $\mu$m, or about 1 $\mu$m to about 10 $\mu$m. In certain aspects of the invention the coating is a parylene coating.

One or more pores are etched in the coating to permit the release of the therapeutic compound from the matrix. The pore size and/or the pore number may be adjusted to achieve the desired release rate for the particular therapeutic agent in the matrix. In certain embodiments of the invention, the pore has a diameter, as measured at the outer surface of the coating, of between about 1 $\mu$m to about 100 $\mu$m, about 1 $\mu$m to about 50 $\mu$m, or about 5 $\mu$m to about 50 $\mu$m. In certain embodiments, the number of pores is between 1 to about 100,000; 1 to about 20,000; 1 to about 10,000; 1 to about 2,000; 1 to about 1,000; 1 to about 100; 1 to about 50; 1 to about 10; 1 to about 8; 1 to about 5; about 5 to about 100; about 5 to about 10; about 10 to about 100,000; about 10 to about 10,000; about 10 to about 2,000; about 10 to about 1,000; about 10 to about 100; about 100 to about 100,000; about 100 to about 10,000; about 100 to about 2,000; or about 100 to about 1,000. In certain aspects, the pores are located only on the surface of the device that is adjacent to the eye such that the therapeutic compound is released unidirectionally onto the eye. For example, where the device is a punctal plug the pore or pores would be located only on the end of the punctal plug that is closest to the front of the eye and exposed to the tears.

In certain aspects, the devices of the present invention deliver a therapeutically effective dose of the therapeutic compound to the subject for about 20 days, about 30 days, about 60 days, about 90 days, about 120 days, about 180 days about 240 days, about 300 days, about 1 year, about 2 years, about 3 years, about 4 years, about 5 years, about 6 years, about 7 years, or about 8 years, or any range derivable therein. In particular embodiments, the devices of the present invention deliver a therapeutically effective dose of the therapeutic compound for at least 90 days.

In certain embodiments, the present invention provides a drug-delivery device comprising: a body comprised of a matrix of a silicone and a prostaglandin, the body having: a shaft portion having a first end and a second end, wherein the shaft portion is configured for insertion through a punctal aperture and positioning in a punctum or lacrimal canaliculus; a head portion attached to the first end of the main portion, wherein the head portion is configured to rest on the exterior of the punctum; and a distal tip portion attached to the second end of the shaft portion; a parylene coating on the surface of the body; at least one pore in the parylene coating, wherein the at least one pore extends from an outer surface of the parylene coating to the surface of the head portion of the body.

In some embodiments, the body further comprises a canalicular extension attached to the distal tip portion, wherein the canalicular extension is configured for insertion through the punctal aperture and the punctum and positioning in the lacrimal canaliculus. A canalicular extension may serve at least two purposes: (1) to improve retention of the plug; and (2) to serve as an additional source of the therapeutic compound. In certain embodiments of the invention, the canalicular extension extends into the nasolacrimal duct and is positioned in both the lacrimal canaliculus and the nasolacrimal duct. In certain aspects of the invention, the canalicular extension has a length L1 and the body has a length L2. The ratio of the length L1 to the length L2 can be about 0.5:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 50:1, or 100:1, or any range derivable therein. In some embodiments, the length of the canalicular extension is between about 1 millimeter (mm) to 30 mm, 1.5 mm to 20 mm, 2 mm to 15 mm, 2 mm to 10 mm, 2 mm to 5 mm, 5 mm to 15 mm, or 5 mm to 10 mm. In three preferred embodiments, the lengths of the canalicular extensions are 8 mm, 15 mm, and 30 mm, respectively. In certain embodiments, the canalicular extension further comprises an integral stylus. The integral stylus may be made of any biocompatible material that provides increased stiffness to the canalicular extension. For example, the integral stylus may be made from stainless steel or a PEEK (oxy-1,4-phenylenoeoxy-1,4-phenylene-carbonyl-1,4-phenylene)polymer.

In certain embodiments, the body further comprises a band or a coating of a bio-expandable polymer on all or a portion of the shaft, distal tip, and/or canalicular extension. The band or coating of bio-expandable polymer will aid in the retention of the implanted device.

In another embodiment, the present invention provides a method of manufacturing an implantable ocular device, comprising: (a) extruding a matrix of a silicone and a prostaglandin to form a body configured for implantation in the punctum, lacrimal canaliculus, sub-conjunctiva space, or anterior sub-Tenon space; (b) depositing a parylene coating on the outer surface of the body; and (c) etching at least one pore in the parylene coating, the pore extending through the parylene coating to the outer surface of the body. In certain aspects, the matrix is extruded to form a punctal plug or a fornix device.

In one embodiment, the present invention provides a method of manufacturing a drug-delivery device, comprising: (a) extruding a matrix of a silicone and a prostaglandin to form a drug-delivery device comprising a body having: (i) a shaft portion having a first end and a second end, wherein the shaft portion is configured for insertion through a punctal aperture and positioning in a punctum or lacrimal canaliculus; (ii) a head portion attached to the first end of the shaft portion, wherein the head portion is configured to rest on the exterior of the punctum; and (iii) a distal tip portion attached to the second end of the shaft portion; (b) depositing a parylene coating on the surface of the body; and (c) etching at least one pore in the parylene coating on the surface of the head portion of the body, wherein the at least one pore extends from an outer surface of the parylene coating to the surface of the head portion of the body.

In certain aspects of the invention the parylene coating is deposited using vapor deposition. In particular embodiments, the pore is etched using oxygen plasma etching or focused ion beam etching. In certain embodiments, the parylene coating is deposited at a thickness of between about 0.5 nanometers (nm) to about 100 micrometers (μm), about 100 nm to about 50 μm, or about 1 μm to about 10 μm. The pore or pores may be etched in the parylene coating using, for example, oxygen plasma etching or focused ion beam etching. In certain aspects of the invention, the opening of the pore is substantially circular. The number of pores and the size of the pores etched in the parylene may be adjusted to achieve the desired release rate for the prostaglandin. In certain aspects, the pores are etched only on the surface of the device that will be adjacent to the eye once the device is implanted. In certain embodiments, the pore has a diameter, as measured at the outer surface of the coating, of between about 1 μm to about 100 μm, about 1 μm to about 50 μm, or about 5 μm to about 50 μm. In some embodiments, 1 to about 100,000; 1 to about 10,000; 1 to about 1,000; 1 to about 100; 1 to about 50; 1 to about 10; 1 to about 8; 1 to about 5; about 5 to about 100; about 5 to about 10; about 10 to about 100,000; about 10 to about 10,000; about 10 to about 1,000; or about 10 to about 100 are etched.

In one embodiment, the present invention provides a method of treating an ocular disorder in a subject comprising: (a) obtaining an implantable ocular device for the sustained release of medication to the eye, the device comprising: (i) a body comprising a matrix of a therapeutic agent and a silicone; (ii) a parylene coating on the outer surface of the body; and (iii) one or more pores extending from the outer surface of the parylene coating to the outer surface of the body; and (b) implanting the device in the punctum, lacrimal canaliculus, sub-conjunctiva space, or anterior sub-Tenon space of the subject. The implantable ophthalmic device may be, for example, a punctal plug, a lacrimal canalicular insert, or a fornix device.

In particular embodiments, the present invention provides a method of treating glaucoma or ocular hypertension in a subject, comprising: (a) obtaining a drug-delivery device comprising: (i) a body comprised of a matrix of a silicone and a prostaglandin, the body having: a shaft portion having a first end and a second end, wherein the shaft portion is configured for insertion through a punctal aperture and positioning in a punctum or lacrimal canaliculus; a head portion attached to the first end of the shaft portion, wherein the head portion is configured to rest on the exterior of the punctum; and a distal tip portion attached to the second end of the shaft portion; (ii) a parylene coating on the surface of the body; (iii) at least one pore in the parylene coating, wherein the at least one pore extends from an outer surface of the parylene coating to the surface of the head portion of the body; (b) implanting the drug-delivery device in the punctum of a subject with glaucoma or ocular hypertension.

In some embodiments, biodegradable microspheres of the drug are formed first and then incorporated into a silicone to form a matrix. Microspheres, microcapsules and nanospheres (collectively, "microspheres") are generally accepted as spherical particles with diameters ranging from approximately 50 nm to 1000 micrometers. They are reservoir devices that come in a variety of different forms, including, but not limited to, porous, hollow, coated, or uncoated forms with a pharmaceutically active agent either incorporated into or encapsulated by polymeric material via numerous known methods. Such known methods include, but are not limited to, spray drying, spinning disk and emulsification methods. Microspheres may be formed from a myriad of polymeric materials selected from, but not limited to, polylactic acids, polyglycolic acids, polylactic-glycolic acids, poly caprolactones, triglycerides, polyethylene glycols, poly orthoesters, poly anhydrides, polyesters, cellulosics and combinations thereof. The amount of drug incorporated or encapsulated in the microsphere is generally between 0.001% and about 50%. In this embodiment, preformed microspheres are incorporated into the drug-delivery device body such that the body comprises a matrix of a silicone and drug-loaded microspheres. The microsphere content incorporated into the drug-delivery device body is generally between 1% and 50%.

The use of the term "or" in the claims is used to mean "and/or" unless explicitly indicated to refer to alternatives only or the alternatives are mutually exclusive.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

In this document (including the claims), the terms "comprise" (and any form of comprise, such as "comprises" and "comprising"), "have" (and any form of have, such as "has" and "having"), and "include" (and any form of include, such as "includes" and "including") are open-ended linking verbs.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention in combination with the detailed description of illustrative embodiments presented below.

FIG. 4 is an illustration of a punctal plug with a canalicular extension.

FIG. 5 is an illustration of the lacrimal duct system of a mammalian eye.

FIG. 8 shows the effect of surface area on AL-6598 release from silicone devices in PBS at 37° C.

DESCRIPTION OF ILLUSTRATIVE EMBODIMENTS

Figures 1, 2:
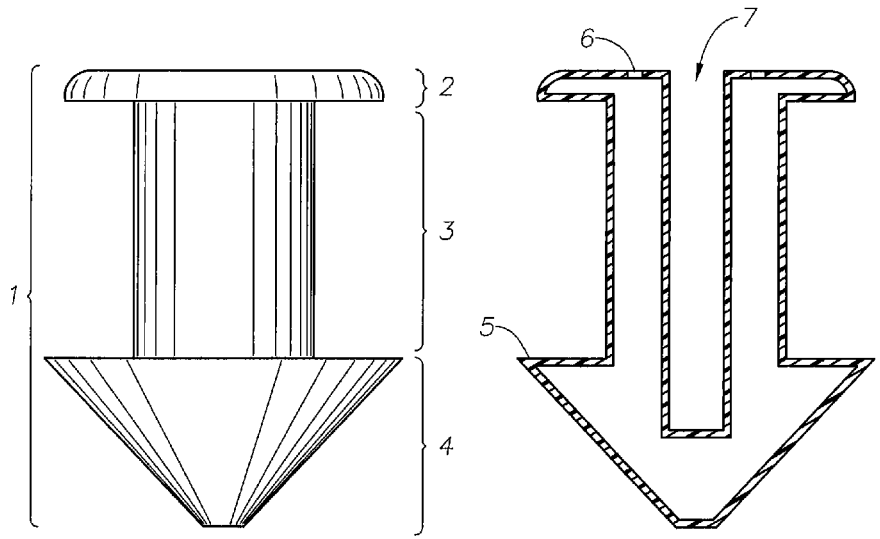
FIG. 1 is a front view of a punctal plug.
FIG. 2 is a cross-sectional view of a punctal plug.
Figures 3A, 3B:
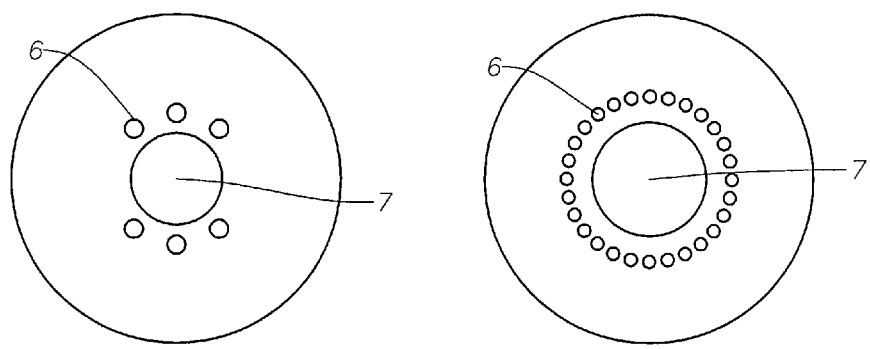
FIGS. 3A and 3B are top views of punctal plugs.

A matrix of silicone and a therapeutic compound may be molded and cured into devices of various shapes that can be useful as drug delivery systems. Such devices can be molded into shapes configured for implantation at essentially any location in the body of a subject. In particular embodiments, a matrix of silicone and prostaglandin is molded into a device for ocular drug delivery for the treatment of glaucoma. In one embodiment, the device is molded by extrusion in which the drug/silicone mixture is pushed through a die with heat such that the cured form takes on the profile of the die.

In vitro and in vivo studies demonstrated that release of prostaglandin from silicone monolithic devices is controlled by the surface area of the device exposed to the environment, although there is a slight drug concentration contribution to the release profile. In vivo studies also demonstrated that the release of prostaglandin from silicone monolithic devices is several times faster than that expected from in vitro results, and that the duration of efficacy of such a device would be too short to be clinically practical unless a major modification of the drug release rate could be achieved. To provide a therapeutic compound/silicone matrix with a drug release profile that is practical as an implantable ocular device, the present invention provides a device comprising: a first member comprising a matrix of a therapeutic compound and a silicone; a parylene coating on the outer surface of the first member; and one or more pores extending from the outer surface of the parylene coating to the outer surface of the first member. Increasing the pore size and/or the number of pores will increase the exposed surface area of the matrix and thus increase the rate at which the therapeutic compound is released. The matrix optionally includes biodegradeable microspheres containing the drug in order to provide additional control of the drug release rate from the matrix.

Preferably, devices of the present invention yield zero-order or near zero-order drug release profiles. In a zero-order reaction, the rate of reaction is a constant. When the limiting reactant is completely consumed, the reaction abruptly stops. (Differential Rate Law: $r=k$; the rate constant, k, has units of mole $L^{-1}$ $sec^{-1}$.) This is distinguished from first-order and second-order reactions. A first-order reaction is where the rate of reaction is directly proportional to the concentration of only one of the reactants and as the reactant is consumed during the reaction, the concentration drops and so does the rate of reaction. (Differential Rate Law: $r=k[A]$; the rate constant, k, has units of $sec^{-1}$). A second-order reaction is where the rate of reaction is directly proportional to the square of the concentration of one of the reactants (or to the concentration of two first order reactants) and decreases rapidly (faster than linear) as the concentration of the reactant decreases (Differential Rate Law: $r=k[A]^2$ or $r=k[A][B]$; the rate constant, k, has units of $L$ $mole^{-1}$ $sec^{-1}$.) Near zero-order describes a situation where there may be an initial brief period where the reaction appears to follow more complex kinetics, but then reverts to zero-order for the majority of the lifetime of the drug release. This is usually the case with devices that have an initial burst of drug—the reaction has an initial rate that appears to change but then maintains a constant rate for the majority of the release.

In one embodiment, the present devices and systems comprise an implantable ocular device configured as a plug for insertion into the punctum and/or lacrimal canaliculus of the eye. FIG. 5 illustrates the lacrimal duct system of a mammalian eye 9. The system includes a lower punctum 11 connected to a lower lacrimal canaliculus 13, and an upper punctum 10 connected to an upper lacrimal canaliculus 12. Canaliculli 12 and 13 are connected to a lacrimal sac 14 and a nasolacrimal duct 15. A lacrimal gland 16 is connected to eye 9 via a lacrimal duct 17. In general, tears are produced by lacrimal gland 16 and are provided to eye 9 via lacrimal duct 17, and tears are drained from eye 9 via punctum 10 and canaliculus 12, punctum 11 and canaliculus 13, and nasolacrimal duct 15.

A variety of plugs for insertion into puncta 10 and 11 and/or canaliculli 12 and 13 are known in the art. Punctal plugs are described in, for example, U.S. Pat. Nos. 3,949,750; 5,283,063; 4,915,684; 4,959,048; 5,723,005; 6,149,684; 6,290,684; 5,417,651; 5,423,777; 5,741,292; 6,027,470; 5,830,171; 6,016,806; 6,041,785; 6,234,175; 6,306,114; and 6,344,047; each of which is incorporated by reference.

One of the drug-delivery devices of the present invention is shown in FIGS. 1-3b. The drug-delivery device comprises: a body 1 comprising a matrix of a silicone and a prostaglandin, the body having an outer surface and being configured to be inserted through a punctal aperture and positioned in a punctum 10 or 11 or lacrimal canaliculus 12 or 13; (b) a parylene coating 5 on a portion of the outer surface of body 1; and (c) at least one pore 6 in parylene coating 5, wherein pore 6 extends from an outer surface of parylene coating 5 to the outer surface of body 1.

In one embodiment, the matrix comprises a silicone and drug-loaded biodegradeable microspheres.

With continued reference to FIGS. 1-3b and with reference to FIG. 5, a punctal plug typically includes a body 1 having a proximal head portion 2, a distal tip portion 4, and a shaft portion 3 connecting proximal head portion 2 and distal tip portion 4. Shaft portion 3 is often smaller in cross-sectional size than proximal head portion 2 and the widest part of distal tip portion 4. A punctal plug is usually inserted, distal tip first, in a punctal aperture and advanced distally in punctum 10 or 11 until proximal head portion 2 is seated on the punctal opening. Punctal plugs may be made available in different sizes corresponding to anatomical puncta and canaliculli of different cross-sectional sizes. Proximal head portion 2 is normally larger than the punctal aperture such that proximal head portion 2 does not pass through the punctal opening and remains exposed in eye 9. Distal tip portion 4 typically has a cross-sectional size to fill punctum 10 or 11 and to anchor punctal plug 1 in place. The occlusion presented by punctal plug 1 deters tear fluid from draining from eye 9 through the punctal opening and the corresponding canalicular canal. Punctal plug 1 may partially or fully occlude punctum 10 or 11. Punctal plugs are typically implanted in the eye using insertion tools (e.g., cannula), and punctal plugs may therefore have an axial passage 7 for releasably engaging the insertion tools to facilitate or guide implantation.

A drug delivery device of the present invention may also be formed as an intracanalicular implant. Intracanalicular implants, which are disposed entirely within the canalicular canal without exposure or protrusion thereof in the eye, are described in, for example, U.S. Pat. Nos. 4,660,546; 5,049, 142; and 5,053,030; 5,163,959; and 5,171,270, each of which is incorporated by reference.

Figure 6:
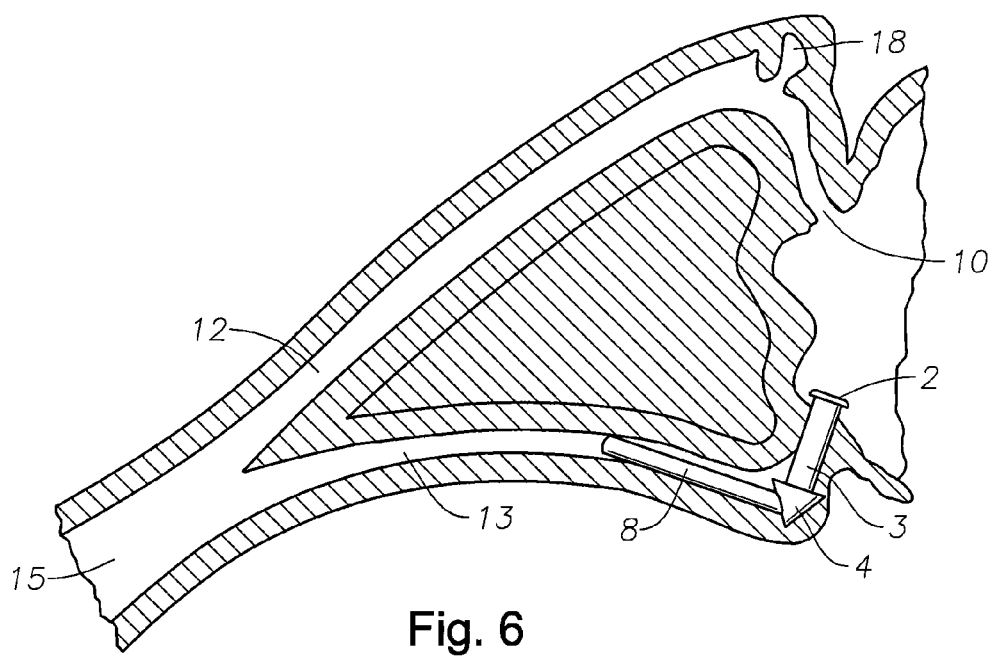
FIG. 6 is an illustration of one of the present medical devices positioned in the lacrimal duct system of a mammalian eye.
Figure 7:
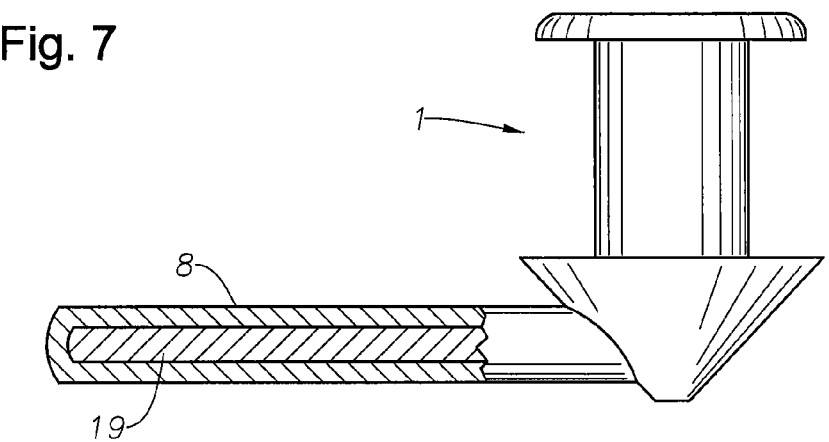
FIG. 7 is a partial cross-section of a punctal plug with a canalicular extension.

With reference to FIGS. 4-6, a punctal plug or intracanalicular implant according to the present invention may also comprise a canalicular extension 8, which extends into the canaliculum 12 or 13. The length of the canalicular extension may be such that it also extends into the nasolacrimal duct 15. The canalicular extension increases the volume of matrix, and thereby the amount of therapeutic compound, in the device. The canalicular extension 8 also serves to increase the retention of the implanted device. In addition, the increased size of a device with the canalicular extension increases the likelihood that the patient will notice if the device becomes dislodged from the punctum. FIG. 6 shows a drug-delivery with a canalicular extension positioned in the lacrimal duct system. In certain embodiments, the canalicular extension comprises an integral stylus 19 as shown in the partial cross-section view in FIG. 7.

With reference to FIG. 4, the canalicular extension 8 can have a length L1 and the body 1 can have a length L2 wherein the ratio of the length L1 to the length L2 can be about 0.5:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 50:1, or 100:1, or any range derivable therein. In some embodiments, the length of the canalicular extension 8 is between about 1 millimeter (mm) to 30 mm, 1.5 mm to 20 mm, 2 mm to 15 mm, 2 mm to 10 mm, 2 mm to 5 mm, 5 mm to 15 mm, or 5 mm to 10 mm. In three preferred embodiments, the lengths of the canalicular extensions are 8 mm, 15 mm, and 30 mm, respectively. The integral stylus 19 may be made of any biocompatible material that provides increased stiffness to the canalicular extension. For example, the integral stylus 19 may be made from stainless steel or a PEEK (oxy-1,4-phenylenoeoxy-1,4-phenylene-carbonyl-1 4-phenylene) polymer.

The implantable ocular devices of the present invention may be used for the topical delivery of eye medications including, for example, glaucoma medication, ocular hypertension medications, antimicrobial medication, anti-inflammatory medication, or dry-eye syndrome medication. In one embodiment, the therapeutic compound is a prostaglandin. The prostaglandin may be a natural or a synthetic prostaglandin. Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins are known in the art including A, B, C, D, E, F, G, I and J-Series prostaglandins (EP 0 561 073 A1). Non-limiting examples of prostaglandins include cloprostenol, fluprostenol, latanoprost, travoprost, and unoprostone.

The devices of the present invention are coated with a non-biodegradable polymer 5 to reduce the exposed surface area of the matrix. In some embodiments of the present invention, the coating is parylene. Parylene is flexible, hydrophobic, substantially impermeable to prostaglandins, highly resistant to chemicals, and can be applied to surfaces by vapor deposition with high conformity and consistency. Parylene also meets FDA Class VI requirements, and has been used in medical device applications to cover implants like pacemakers and shunts. Parylene is the generic name for members of a unique polymer series. The basic member of the series, called Parylene N, is poly-para-xylylene, a linear, highly crystalline material. Other members of the series include Parylene C, Parylene D, and Parylene F.

Methods for depositing parylene coatings on silicone are known in the art. For example, a parylene coating may be vapor deposited on a silicone device of the present invention by placing the device in a vacuum deposition chamber and drawing a vacuum in the chamber to approximately 0.1 torr. A parylene dimer (di-para-xylylene) is vaporized at approximately 150° C. A pyrolysis of the monomer (para-xylylene) is then affected at approximately 680° C. and 0.5 torr. The monomer then enters the deposition chamber at approximately room temperature (approximately 25° C.) and is adsorbed and polymerizes onto the silicone device. The resultant coating is conformal, covering all exposed surfaces equally.

Parylene coatings may be deposited in layers with thicknesses of as little as about 0.5 nanometers up to several millimeters. Once the coating has been applied to the implantable ocular device, one or more pores may be etched in the coating to permit the release of the therapeutic compound from the matrix by providing an opening in the coating through which the therapeutic compound can diffuse. Alternatively, the pores may be created during the parylene deposition process by masking the surface of the device at positions where there pores are desired. The pore size and/or the pore number may be adjusted to achieve the desired release rate for the particular therapeutic agent in the matrix. As mentioned above, the release of therapeutic compound from the silicone matrix was controlled by the exposed surface area of the matrix. Thus, increasing the pore size and/or the number of pores will increase the exposed surface area of the matrix and thus increase the rate at which the therapeutic compound is released from the matrix. Furthermore, the pores may be positioned on the device such that the therapeutic compound is released unidirectionally onto the eye. For example, where the device is a punctal plug the pore or pores would be located on the head portion of the punctal plug that is exposed to the tears.

The pores may be etched into the coating of the device using, for example, a focused ion beam (FIB) or an oxygen plasma etching process (see e.g. Meng and Tai, 2005; incorporated by reference). It is preferable to etch the pores on a substantially flat surface of the device as it makes the etching process more consistent. FIB uses a focused beam of gallium ions to sputter atoms from the surface of the material being etched. Because parylene is not conductive, the impinging gallium ions tend to "charge up" the parylene layer over time, which may eventually inhibit milling. To overcome this charging effect, the parylene surface may be coated with a thin layer of conductive material (e.g., metal or carbon) or provided with a temporary contact to a conductive material. Focused ion beams have a Gaussian profile. As a result, the milled holes have sloping sidewalls (i.e., the holes get smaller as they go deeper). Based on studies of FIB etching through a 5 µm layer of parylene deposited on a silicone die, it was determined that an aspect ratio of under about 5:1 (e.g., a 1 µm diameter pore, as measured at the outer surface of the parylene coating, through a 5 µm thick layer of parylene) is needed to form a pore that extends completely through the parylene layer.

Oxygen plasma etching is a dry-etching process that takes place in an oxygen plasma environment where oxygen radicals are formed. Typical conditions for oxygen plasma etching include: an oxygen pressure of from about 10 to about 500 militorr, and an RF power of from about 100 to about 200 watts. Another way to etch pores in the coating of the device is with a scanning electron microscope probe.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The Release of Prostaglandin from a Silicone Matrix is Controlled by the Surface Area of the Matrix Exposed to the Environment To study the effect of surface area on the release of prostaglandin from a silicone matrix, prostaglandin release from silicone dies of three different sizes was measured. The largest silicone die measured 10 mm×10 mm×1 mm. A ½ size device (10 mm×5 mm×1 mm) and a ¼ size device (5 mm×5 mm×1 mm) were also used in this study. Each silicone die contained 10% AL-6598, which is a DP class prostaglandin analogue. The silicone die were placed in phosphate buffered saline (PBS) at 37° C. and the amount of AL-6598 released was measured. As shown in FIG. 8, the release of AL-6598 was dependent on the size of the silicone die with the larger surface area resulting in the more rapid drug release.

EXAMPLE 2

Parylene Coating and Etching

Two silicone die (10 mm×10 mm×1 mm) were coated with 5 µm of parylene using a vapor deposition process. To coat the silicone die, the die were placed in a vacuum deposition chamber and a vacuum was drawn in the chamber to approximately 0.1 torr. A parylene dimer (di-para-xylylene) was vaporized at approximately 150° C. Then pyrolysis of the monomer (para-xylylene) was affected at approximately 680° C. and 0.5 torr. The monomer then entered the deposition chamber at approximately room temperature (approximately 25° C.) and was adsorbed and polymerized onto the silicone die.

The parylene coated silicone die were then milled using FIB. Pores of 1 µm and 1.5 µm were milled through the 5 µm thick layer of parylene on one of the silicone die. Each pore was milled within 30 seconds. 1000 Angstroms of metal were deposited on the surface of the parylene to prevent the "charging up" of the parylene layer by the impinging gallium ions during the FIB etching process. Focused ion beams have a Gaussian profile. As a result, the pores have sloping sidewalls. To determine the smallest feature size that can be etched through the parylene, multiple pores with diameters of 0.5 µm, 1 µm, 1.5 µm, 3 µm, and 5 µm were milled in the 5 µm parylene layer of the other silicone die. The 0.5 µm pore did not extend completely through the parylene layer because of the sloping sidewalls, whereas the 1 µm and larger pores did extend completely through the parylene layer. From this study it can be seen that pores with an aspect ratio under 5:1 can be milled through the parylene layer using the FIB process.

EXAMPLE 3

Punctal Plug Containing Microspheres

Travoprost is prepared as a polylactic acid microsphere having an average size of 100 nm-1 µm. The microspheres contain 10% travoprost by weight. 10 g of drug-loaded microspheres are added to 45 g of silicone Part A in a first Semco press tube and mixed on a Flack Tek mixer at 1500 RPM for 30 seconds. 45 g of silicone Part B are added to a second Semco press tube. Both press tubes are placed on an injection assembly of a premetered silicone press and injected into a steel mold to make a silicone die having the desired punctal plug shape and dimensions. After curing, the silicone device is coated with parylene and etched according to the procedures described in Example 2.

\* \* \*

All of the compositions and methods disclosed and claimed herein can be made and executed without undue experimentation in light of the present disclosure. While the devices and methods of this invention have been described in terms of particular embodiments, it will be apparent to those of skill in the art that variations may be applied to the devices and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. The appended claims are not to be interpreted as including means-plus-function limitations, unless such a limitation is explicitly recited in a given claim using the phrase(s) "means for" and/or "step for," respectively.

REFERENCES

The following references, to the extent that they provide exemplary procedural or other details supplementary to those set forth herein, are specifically incorporated herein by reference.

U.S. Pat. No. 3,949,750
U.S. Pat. No. 3,949,750
U.S. Pat. No. 4,660,546
U.S. Pat. No. 4,690,931
U.S. Pat. No. 4,915,684
U.S. Pat. No. 4,959,048
U.S. Pat. No. 5,049,142;
U.S. Pat. No. 5,053,030
U.S. Pat. No. 5,053,030
U.S. Pat. No. 5,151,444
U.S. Pat. No. 5,163,959
U.S. Pat. No. 5,171,270
U.S. Pat. No. 5,283,063
U.S. Pat. No. 5,296,504
U.S. Pat. No. 5,352,708
U.S. Pat. No. 5,417,651
U.S. Pat. No. 5,422,368
U.S. Pat. No. 5,423,777
U.S. Pat. No. 5,469,867
U.S. Pat. No. 5,723,005
U.S. Pat. No. 5,741,292
U.S. Pat. No. 5,830,171
U.S. Pat. No. 5,889,052
U.S. Pat. No. 6,016,806
U.S. Pat. No. 6,027,470
U.S. Pat. No. 6,041,785
U.S. Pat. No. 6,149,684
U.S. Pat. No. 6,196,993
U.S. Pat. No. 6,234,175
U.S. Pat. No. 6,290,684
U.S. Pat. No. 6,306,114
U.S. Pat. No. 6,344,047
U.S. Patent 60/203,350
U.S. Patent Publn. 2003/0143280
U.S. Patent Publn. 2004/0013704
U.S. Patent Publn. 2005/0232972
U.S. Patent Publn. 2006/0020248
PCT Appln. WO 2004/066980
PCT Appln. WO 2006/031658
PCT Appln. WO 94/13275
PCT Appln. WO 99/37260
EP 0 561 073 A1

Meng and Tai, "Parylene Etching Techniques for Microfluidics and BioMEMS," *Micro Electro Mechanical Systems,* 30:568-571, 2005

What is claimed is:

1. A drug-delivery device comprising:
    (a) a body comprising a matrix of a silicone and an ophthalmic drug dispersed throughout the matrix, the body being a monolithic structure having an outer surface and being configured to be inserted through a punctal aperture and positioned in a punctum or lacrimal canaliculus;
    (b) a parylene coating covering the outer surface of the body, the parylene coating being substantially impermeable to the drug; and
    (c) at least one pore in the parylene coating, wherein the at least one pore extends from an outer surface of the parylene coating to the surface of the body;
    wherein the parylene coating covers all surfaces of the outer surface of the body with the exception of the surface of the body exposed by the at least one pore;
    wherein the ophthalmic drug is a glaucoma medicament.

2. The drug-delivery device of claim 1, wherein the body comprises:
    (a) a shaft portion having a first end and a second end, wherein the shaft portion is configured for insertion through a punctal aperture and positioning in a punctum or lacrimal canaliculus;
    (b) a head portion attached to the first end of the shaft portion, wherein the head portion is configured to rest on the exterior of the punctum; and
    (c) a distal tip portion attached to the second end of the shaft portion.

3. The drug delivery device of claim 1, wherein the glaucoma medicament is a prostaglandin.

4. The drug-delivery device of claim 3 wherein the prostaglandin is cloprostenol, fluprostenol, latanoprost, travoprost, or unoprostone.

5. The drug delivery device of claim 3, wherein the concentration of the prostaglandin in the matrix is 0.5% to 15% by weight.

6. The drug delivery device of claim 3, wherein the concentration of the prostaglandin in the matrix is 1% to 10% by weight.

7. The drug-delivery device of claim 1, wherein the parylene coating is 1 μm to 20 μm thick.

8. The drug-delivery device of claim 1, wherein the parylene coating is 5 μm to 15 μm thick.

9. The drug-delivery device of claim 2, wherein the body further comprises a canalicular extension attached to the distal tip portion of the body, wherein the canalicular extension is configured for insertion through the punctal aperture and the punctum and positioning in the lacrimal canaliculus.

10. The drug-delivery device of claim 9, wherein the canalicular extension has a length L1 and the body has a length L2, wherein the ratio of the length L1 to the length L2 is 2:1 to 10:1.

11. The drug-delivery device of claim 9, wherein the canalicular extension is configured for positioning in both the lacrimal canaliculus and a nasolacrimal duct.

12. The drug delivery device of claim 2 wherein the at least one pore extends to the surface of the body at the head portion.

13. The drug delivery device of claim 1, wherein the glaucoma medicament is travoprost and wherein the silicone operates in conjunction with the at least one pore to release the travoprost at a therapeutically effective dose for period of 60 to 240 days.

14. The drug delivery devices of claim 1 wherein a length L1 of the canalicular extension is between 5 and 15 millimeter.

15. A drug-delivery device comprising:
  (a) a body comprising a matrix of a silicone and an ophthalmic drug dispersed throughout the matrix, the body having an outer surface and being configured to be inserted through a punctal aperture and positioned in a punctum or lacrimal canaliculus, wherein the body is a monolithic structure that includes:
    i. a shaft portion having a first end and a second end, wherein the shaft portion is configured for insertion through a punctal aperture and positioning in a punctum or lacrimal canaliculus;
    ii. a head portion attached to the first end of the shaft portion, wherein the head portion is configured to rest on the exterior of the punctum; and
    iii. a distal tip portion attached to the second end of the shaft portion;
  (b) a parylene coating covering the outer surface of the body, the parylene coating being substantially impermeable to the drug; and
  (c) at least one pore in the parylene coating, wherein the at least one pore extends from an outer surface of the parylene coating to the surface of the head portion of the body;
  wherein the parylene coating covers all surfaces of the outer surface of the body with the exception of the surface of the head portion exposed by the at least one pore;
  wherein the ophthalmic drug is a glaucoma medicament.

16. The drug-delivery device of claim 15, wherein the glaucoma medicament is a prostaglandin.

17. The drug-delivery device of claim 15 wherein the body further comprises a canalicular extension attached to the distal tip portion of the body, wherein the canalicular extension is configured for insertion through the punctal aperture and the punctum and positioning in the lacrimal canaliculus and wherein the canalicular extension has a length L1 and the body has a length L2, wherein the ratio of the length L1 to the length L2 is 2:1 to 10:1 and wherein the length L1 of the canalicular extension is between 5 and 15 millimeter.

18. The drug delivery devices of claim 15, wherein the glaucoma medicament is travoprost and wherein the silicone operates in conjunction with the at least one pore to release the travoprost at a therapeutically effective dose for period of 60 to 240 days.

19. A drug-delivery device comprising:
  (a) a body comprising a matrix of a silicone and an ophthalmic drug dispersed throughout the matrix, the body having an outer surface and being configured to be inserted through a punctal aperture and positioned in a punctum or lacrimal canaliculus, wherein the body is a monolithic structure that includes:
    i. a shaft portion having a first end and a second end, wherein the shaft portion is configured for insertion through a punctal aperture and positioning in a punctum or lacrimal canaliculus;
    ii. a head portion attached to the first end of the shaft portion, wherein the head portion is configured to rest on the exterior of the punctum; and
    iii. a distal tip portion attached to the second end of the shaft portion;
  (b) a parylene coating covering the outer surface of the body, the parylene coating being substantially impermeable to the drug; and
  (c) at least one pore in the parylene coating, wherein the at least one pore extends from an outer surface of the parylene coating to the surface of the head portion of the body;
  wherein the parylene coating covers all surfaces of the outer surface of the body with the exception of the surface of the head portion exposed by the at least one pore and wherein the ophthalmic drug is travoprost and wherein the silicone operates in conjunction with the at least one pore to release the travoprost at a therapeutically effective dose for period of 60 to 240 days.

20. The drug-delivery device of claim 2, wherein the body further comprises a canalicular extension attached to the distal tip portion of the body, wherein the canalicular extension is configured for insertion through the punctal aperture and the punctum and positioning in the lacrimal canaliculus and wherein the canalicular extension has a length L1 and the body has a length L2, wherein the ratio of the length L1 to the length L2 is 2:1 to 10:1 and wherein the length L1 of the canalicular extension is between 5 and 15 millimeter.

21. The drug delivery device of claim 9 wherein the canalicular extension includes a stylus for providing increased stiffness to the canalicular extension.

22. The drug delivery device of claim 17 wherein the canalicular extension includes a stylus for providing increased stiffness to the canalicular extension.

23. The drug delivery device of claim 20 wherein the canalicular extension includes a stylus for providing increased stiffness to the canalicular extension.

\* \* \* \* \*